US00PP30502P2

(12) United States Plant Patent
Van Swieten

(10) Patent No.: US PP30,502 P2
(45) Date of Patent: May 14, 2019

(54) ***PHALAENOPSIS* ORCHID PLANT NAMED 'PHALGALDAN'**

(50) Latin Name: ***Phalaenopsis* hybrid**
Varietal Denomination: PHALGALDAN

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 15/932,588

(22) Filed: Mar. 19, 2018

(51) Int. Cl.
*A01H 5/02* (2018.01)

(52) U.S. Cl.
USPC ..... Plt./311

(58) Field of Classification Search
USPC ..... Plt./311
See application file for complete search history.

*Primary Examiner* — Susan McCormick Ewoldt
(74) *Attorney, Agent, or Firm* — Jondle & Associates, P.C.

(57) ABSTRACT

A new and distinct variety of *Phalaenopsis* plant named 'PHALGALDAN', particularly characterized by having small white flowers with a white lip, 1 to 3 peduncles that are medium long, leaves that are oblong, and is propagated by meristem tissue culture, is disclosed.

3 Drawing Sheets

Genus and species: *Phalaenopsis* hybrid.
Variety denomination: 'PHALGALDAN'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALGALDAN'.

The new *Phalaenopsis* plant is a product of a planned breeding program conducted by the inventor in Bleiswijk, The Netherlands. The objective of this breeding program was to create a new *Phalaenopsis* plant with numerous attractive small white flowers with a white lip, suitable for potted plant production.

The new *Phalaenopsis* plant 'PHALGALDAN' is a result of cross-pollination made by the inventor in September 2008 in Bleiswijk, The Netherlands of the proprietary female, or seed parent, *Phalaenopsis* hybrid '01-8917' (unpatented) with the proprietary male, or pollen parent, *Phalaenopsis* hybrid '01-8918' (unpatented).

The new *Phalaenopsis* was selected by the inventor as a single plant within the progeny of the stated cross-pollination in a controlled greenhouse in Bleiswijk, The Netherlands in September 2011. Asexual reproduction of the new *Phalaenopsis* plant by meristem tissue culture since 2014 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Apr. 24, 2017. 'PHALGALDAN' has not been made publicly available or sold anywhere in the world more than one year prior to the effective filing dale of this application.

SUMMARY OF THE INVENTION

The following are the most outstanding and distinguishing characteristics of this new cultivar when grown under normal horticultural practices in Bleiswijk, The Netherlands and can be used to distinguish 'PHALGALDAN' as a new and distinct variety of *Phalaenopsis* plant.

1) Small white flowers with a white lip;
2) 1 to 3 peduncles;
3) Peduncle is medium long; and
4) Shape of the leaf is oblong.

DESCRIPTION OF THE PHOTOGRAPHS

This new *Phalaenopsis* plant is illustrated by the accompanying photographs which show the overall plant habit including blooms, buds and foliage of the plant; the colors shown are as true as can be reasonably obtained by conventional photographic procedures. The photographs were taken in a greenhouse in Bleiswijk, The Netherlands, from 50-week old plants in February 2018. Colors in the photographs may differ from the color values cited in the detailed botanical description, which accurately describe the actual colors of the new variety.

DESCRIPTION OF THE NEW VARIETY

Figure 1:
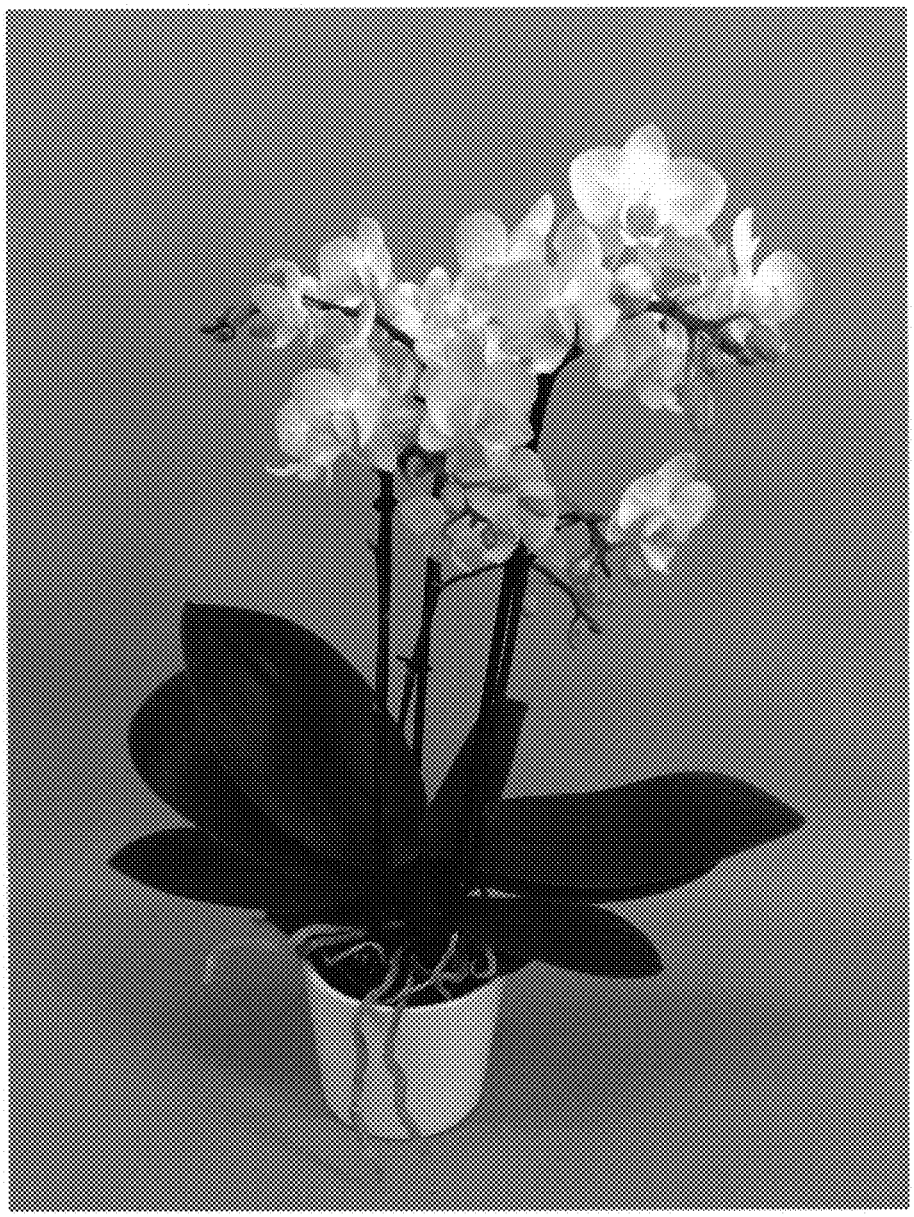
FIG. 1 shows the overall plant habit, including blooms, buds and foliage of 'PHALGALDAN'.
Figure 2:
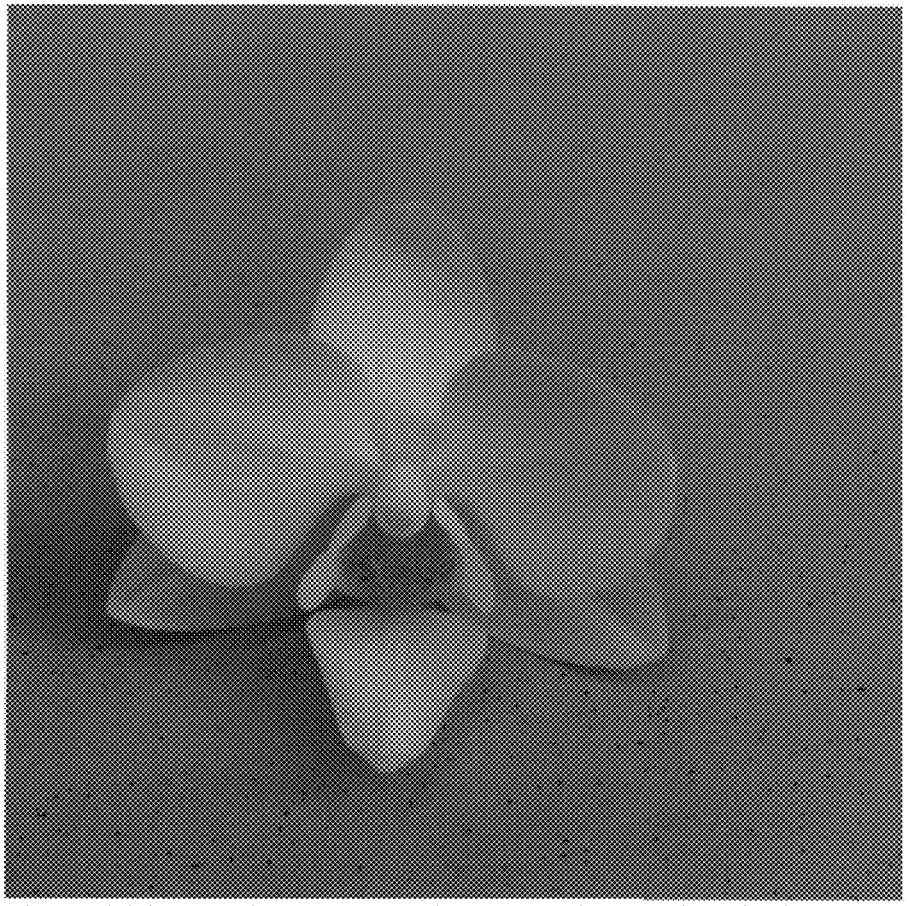
FIG. 2 shows a close-up of a flower of 'PHALGALDAN'.
Figure 3:
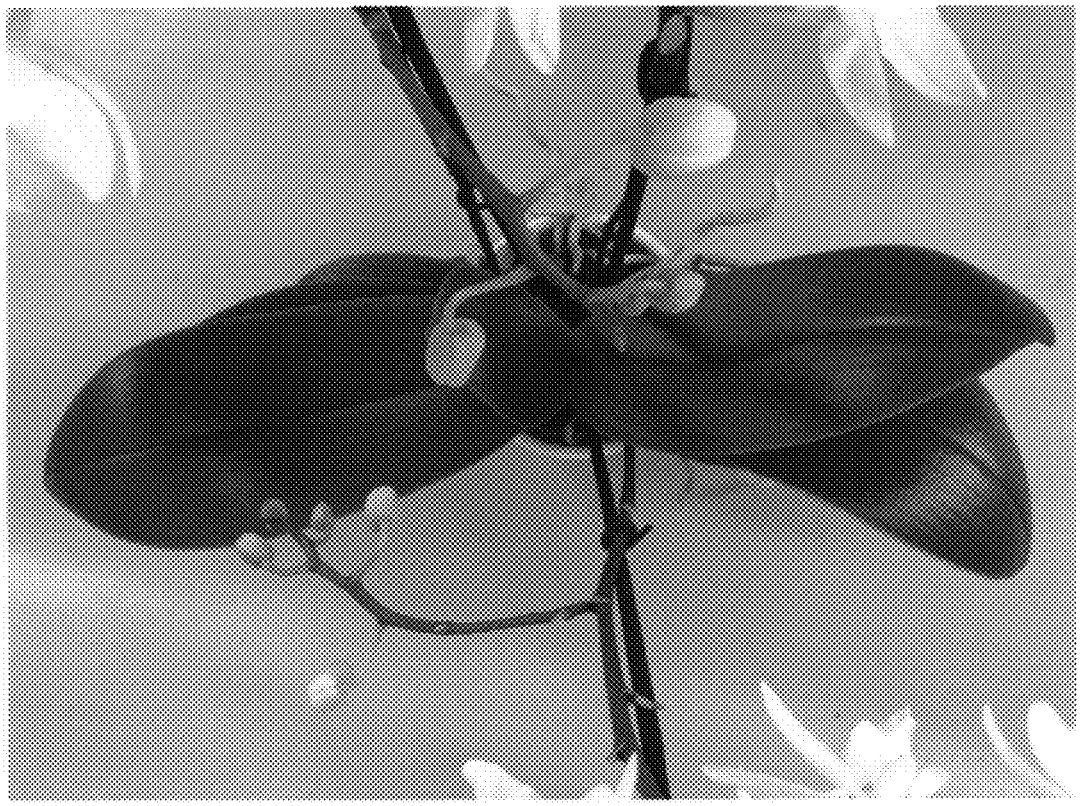
FIG. 3 shows an overhead view of the buds and leaves of 'PHALGALDAN'.

The following detailed description sets forth the distinctive characteristics of 'PHALGALDAN'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in February 2018 on flowering plants which were planted in 6 centimeter (diameter) pots. After in-vitro propagation, the plants were directly transplanted to 6 centimeter (diameter) pots and grown in a greenhouse between 27° C. to 29° C. for 32 weeks, continued by a cooling period of 6 weeks between 18° C. to 20° C. and 12 weeks in a greenhouse of 21° C. Flowering occurs after 50-weeks in a 6 centimeter pot.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALGALDAN'.

Parentage:

*Female parent*.—*Phalaenopsis* cultivar '01-8917' (unpatented).

*Male parent*.—*Phalaenopsis* cultivar '01-8918' (unpatented).

Propagation:

*Type*.—Meristem tissue culture.

Roots:

*Root description*.—Greyed-green colored roots (RHS 190B/C) with branching lateral roots having light green (RHS 144B) colored root tips.

Plant:

*Commercial crop time to flowering*.—Following asexual propagation (in-vitro), the plants are directly transplanted to 6 cm pots and the plants are finished after 48 to 50 weeks.

*Growth habit of peduncle*.—Standard, green leaves, raceme to panicle.

*Height* (*from soil level to top of inflorescence*).—Approximately 30.0 cm to 35.0 cm.

*Width* (*measured from leaf tips*).—About 30.0 cm to 32.0 cm.

*Vigor*.—Moderate.

Leaves:

*Mature leaves*.—Quantity per plant: 7 to 9 leaves are produced before flowering. Length (fully expanded): 15.0 cm to 18.0 cm. Width: 6.5 cm to 7 5 cm. Shape: Oblong. Base shape: Moderately elongated to elongated. Apex: Acute unequal. Leaf blade angle with the petiole (measured from the horizontal position): Between 10 degrees and 25 degrees. Leaf margin: Entire. Color: Upper surface: RHS 146A. Lower surface: Mix of RHS 146B and diluting RHS 187A. Texture: Smooth upper surface. Thickness: 2.0 mm to 2.3 mm. Venation: Pattern: Parallel. Color of the midvein: Upper surface: RHS 187A. Lower surface: RHS 187B.

Peduncle:

*Quantity per plant*.—1 to 3.

*Number of flowers per peduncle*.—13 to 23.

*Length*.—30.0 cm to 35.0 cm.

*Diameter*.—3.2 mm to 3.4 mm.

*Strength*.—Moderate.

*Aspect*.—Upright to slightly pendant.

*Texture*.—Smooth.

*Color*.—Mix of brown (RHS 200C) and green (RHS 146B).

*Internode length*.—4.0 cm to 4.5 cm.

*Callosities*.—None.

Inflorescence description:

*Appearance*.—Upright to slightly pendant, raceme to panicle inflorescence with bilaterally symmetrical flowers that open in succession beginning with the lowermost flower.

*Inflorescence size*.—Height (from base to tip): 140.0 mm to 190.0 mm.

*Flowering time*.—First flowers can be expected 10 to 11 months after planting in a 6 cm (diameter) pot.

*Flower*.—Height: 38.0 mm to 40.0 mm. Diameter: 41.0 mm to 43.0 mm. Depth of lip: 14.0 mm to 16.0 mm.

*Flower longevity*.—On the plant: 8 to 14 weeks.

*Fragrance*.—Absent.

*Flower bud*.—Average size: Medium. Length: 13.0 mm to 15.0 mm. Width: 10.0 mm to 12.0 mm. Shape: Egg shaped. Color: Light green (RHS 145C).

*Petals*.—Arrangement: Open/free. Shape: Semi-circular. Apex: Rounded asymmetric. Margin: Entire. Length (from base to tip): 20.0 mm to 22.0 mm. Width: 21.0 mm to 23.0 mm. Color (when fully opened): Upper surface: Basic color: White (RHS NN155C). Over color: Absent. Lower surface: Basic color: White (RHS NN155C). Over color: Middle vein very light purple (RHS 76C).

*Dorsal sepal*.—Shape: Elliptic. Apex: Obtuse symmetric. Margin: Entire. Length (from base to tip): 22.0 mm to 24.0 mm. Width: 15.0 mm to 17.0 mm. Color (when fully opened): Upper surface: Basic color: White (RHS NN155C). Over color: Absent. Lower surface: Basic color: White (RHS NN155C). Over color: Middle vein very light purple (RHS 76D).

*Lateral sepals*.—Shape: Ovate. Apex: Obtuse asymmetric. Margin: Entire. Length (from base to tip): 22.0 mm to 24.0 mm. Width: 14.0 mm to 16.0 mm. Color (when fully opened): Upper surface: Basic color: White (RHS NN155C). Over color: Slightly light green (RHS 145D) at the base. Lower surface: Basic color: White (RHS NN155C). Over color: Very light green (RHS 145D); very light purple tips (RHS 76B).

*Labellum* (*lip*).—Whiskers: Present. Length of whiskers: 1.0 mm to 3.0 mm. Color of whiskers: White (RHS NN155C). Pubescence on the lip: Absent.

*Lateral lobe*.—Shape: Type IV (as described in the International Union for the Protection of New Varieties of Plants (UPOV) Test Guidelines for *Phalaenopsis*); weakly spatulate. Margin: Slightly undulated. Length: 11.0 mm to 13.0 mm. Width: 7.0 mm to 9.0 mm. Color: White (RHS NN155C); slightly light yellow (RHS 9C) at the base with spots (RHS 174C).

*Apical lobe*.—Shape: Triangular. Margin: Entire. Length: 14.0 mm to 16.0 mm. Width: 12.0 mm to 14.0 mm. Color: White (RHS NN155C).

*Callus*.—Average size: Small. Height: 0.3 cm to 0.4 cm. Length: 0.4 cm to 0 5 cm. Width: 0.3 cm to 0.4 cm. Color: Yellow (RHS 9B) dotted (RHS 173A).

Reproductive organs:

*Column*.—Length: 7.0 mm to 9.0 mm. Diameter: 3.2 mm to 3.4 mm. Color: White (RHS NN155C).

*Pollinia*.—Quantity: 2. Diameter: 0.6 mm to 0.8 mm. Color: Orange (RHS 24A).

*Ovary*.—Length: 9.0 mm to 11.0 mm. Diameter: 1.3 mm to 1.6 mm.

*Pedicel*.—Length: 25.0 mm to 27.0 mm. Diameter: 1.6 mm to 1.8 mm. Color: Light green (RHS 145C) at the base and pinkish white (RHS N155B) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

The female parent plant of 'PHALGALDAN', cultivar '01-8917' (unpatented), is no longer in existence, so a meaningful comparison cannot be made.

The male parent plant of 'PHALGALDAN', cultivar '01-8918' (unpatented), is no longer in existence, so a meaningful comparison cannot be made.

'PHALGALDAN' is most similar to the commercial *Phalaenopsis* plants named 'PHALDUXI' (U.S. Plant Pat. No. 25,680) and 'PHALDUEL' (U.S. Plant Pat. No. 28,256). 'PHALGALDAN' differs from the commercial variety 'PHALDUXI' in that 'PHALGALDAN' has a white apical lobe, peduncles that are a mix of brown and green, and a rounded petal apex, whereas 'PHALDUXI' has a white apical lobe with yellow shade, green peduncles, and a mucronate petal apex. Additionally, 'PHALGALDAN' has shorter whiskers, longer leaves, and smaller flowers than 'PHALDUXI'.

'PHALGALDAN' differs from the commercial variety 'PHALDUEL' in that 'PHALGALDAN' has a white apical lobe and peduncles that are a mix of brown and green, whereas 'PHALDUEL' has a white apical lobe with yellow-green toward the callus and peduncles that are green and slightly greyed purple. Additionally, 'PHALGALDAN' has shorter whiskers, longer leaves, and smaller flowers than 'PHALDUEL'.

I claim:

1. A new and distinct variety of *Phalaenopsis* plant named 'PHALGALDAN', substantially as described and illustrated herein.

* * * * *